United States Patent
Le Gros et al.

(10) Patent No.: US 8,062,645 B2
(45) Date of Patent: Nov. 22, 2011

(54) SALMONELLA VACCINE

(75) Inventors: François-Xavier Le Gros, Saint Genis Laval (FR); Stephane Lemiere, Lyons (FR)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 11/953,472

(22) Filed: Dec. 10, 2007

(65) Prior Publication Data

US 2008/0220022 A1 Sep. 11, 2008

Related U.S. Application Data (60) Provisional application No. 60/869,524, filed on Dec. 11, 2006.

(51) Int. Cl.
| | | |
|---|---|---|
| *A61K 39/112* | (2006.01) | |
| *A61K 39/00* | (2006.01) | |
| *A61K 39/116* | (2006.01) | |
| *C12P 1/00* | (2006.01) | |

(52) U.S. Cl. ............... 424/258.1; 424/184.1; 424/203.1; 435/41

(58) Field of Classification Search .................. None
See application file for complete search history.

(56) References Cited

OTHER PUBLICATIONS

Cerquetti et al (Vaccine 18, 2000, p. 1114-1145).*
Muir et al (Poultry Science, 1998, vol. 77, p. 1874-1883).*
Zhang-Barber et al (Vaccine 17, 1999, p. 2538-2545).*
Suphabphant et al (Avian Diseases, Jul.-Sep. 1983, vol. 37, No. 3, p. 602-615).*
Barrow P A et al: "Vaccination against *Salmonella* infections in food animals: rationale, theoretical basis and practical application" 2000, A. Wray & C. Wray, Salmonella in Domestic Animals (pp. 323-339).
Chacana P A et al: "Protection conferred by a live *Salmonella enteritidis* vaccine against fowl typhoid in laying hens" Avian Diseases, American Association of Avian Pathologists, Kennet Sq., PA, US, vol. 50, No. 2, Jun. 2006, pp. 280-283.
Lillehoj E P et al: "Vaccines Against the Avian Enteropathogens Eimeria, Cryptosporidium and *Salmonella*" Animal Health Research Reviews, CA81 Publishing, GB, vol. 1, No. 1, Jun. 2000, pp. 47-65.
Nassar T J et al: "Use of Live and Inactivated *Salmonella enteritidis* Phage Type 4 Vaccines to Immunise Laying Hens Against Experimental Infection" Revue Scientifique Ettechnique—Office International Des Pizooties / Scientific and Technical Review—International Office of Epizootics, Office International Des Epizooties, Paris, FR, vol. 13, No. 3, 1994, pp. 855-867.
Smith H W: "The use of live vaccines In experimental *Salmonella* gallinarum infection in chickens with observations on their interference effect." The Journal of Hygiene Sep. 1956, vol. 54, No. 3, Sep. 1956, pp. 419-432.
Wigley Paul et al: "Oral infection with the *Salmonella* enterica serovar Gallinarum 9R attenuated live vaccine as a model to characterise immunity to fowl typhoid in the chicken" BMC Veterinary Research, Biomed Central, London, GB, vol. 1, No. 1, Sep. 12, 2005,.p. 2.
Zhang-Barber L et al: "Vaccination for control of *Salmonell a* in poultry" Vaccine, Butterworth Scientific. Guildford, GB, vol. 17, No. 20-21, Jun. 4, 1999, pp. 2538-2545.

* cited by examiner

*Primary Examiner* — Vanessa L. Ford
(74) *Attorney, Agent, or Firm* — Judy Jarecki-Black; Ruoying Chen; Merial Limited (57) ABSTRACT

The present invention relates to the field of vaccination against *Salmonella* in animals, particularly avian animals. The present invention also encompasses kits and uses of *Salmonella* immunogenic compositions or vaccines. The present invention further relates to methods and compositions comprising at least one primo-administration of an attenuated immunogenic composition or vaccine, comprising a pharmaceutically or veterinarily acceptable excipient, diluent or vehicle and at least one attenuated *Salmonella*, administered to an avian animal before at least one boost-administration of an inactivated immunogenic composition or vaccine, comprising a pharmaceutically or veterinarily acceptable excipient, diluent or vehicle, and at least one inactivated *Salmonella*.

18 Claims, 2 Drawing Sheets

SALMONELLA VACCINE

INCORPORATION BY REFERENCE

This application claims benefit of U.S. provisional patent application Ser. No. 60/869,524 filed Dec. 11, 2006.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the field of vaccination against *Salmonella* in animals, particularly avian animals. The present invention also encompasses kits and uses of *Salmonella* immunogenic compositions or vaccines.

BACKGROUND OF THE INVENTION

*Salmonella* spp. are facultative intracellular pathogens causing localized or systemic infections, in addition to a chronic asymptomatic carrier state. They are of worldwide economic and public health significance. In poultry, fowl typhoid and pullorum disease continue to cause economic losses in those parts of the world where the poultry industries are continuing to intensify and where open sided housing is common. A number of serotypes that cause human gastroenteritis are also increasing. The costs or impracticality of improvements in hygiene and management together with increasing problems of antibiotic resistance indicates that vaccination in poultry will become more attractive as an adjunct to existing control measures (Zhang-Barber L. et al., Vaccine, 1999, 17(20-21): 2538-45).

*Salmonella* is one of the major causes of food-borne illnesses in humans. According to the Commission's report on zoonoses (European Commission: Trends and sources of zoonotic infections in animals, feed, food and man in the European Union and Norway in 2003), 135,546 human cases of salmonellosis have been reported in 2003 by the 15 Member States of the European Union and Norway.

The poultry industry, especially in Europe and in the US, is under strong pressure from health authorities and consumers to reduce the risks of human contamination with *Salmonella* of poultry origin, particularly salmonellosis (pathogen reduction and HACCP in the US, Council Directive 92/117/EEC in the EU).

As *Salmonella* infects many animal populations (e.g., mammalian, avian), the risk of suffering salmonellosis always exists, whatever the country, the season or the food handling practices.

The zoonotic *Salmonella* spp. causes of human gastrointestinal infection have been treated with existing antimicrobials. Since the early 1990s, strains of *Salmonella* resistant to a range of antimicrobials have appeared, making the treatment of infection less efficient and increasing the human risk of contracting a gastrointestinal infection caused by *Salmonella* spp.

As in previous years, *Salmonella enterica* subspecies *enterica* serovar Enteritidis (*Salmonella* Enteritidis) dominated, causing 61.8% (2002: 67.1%) of all notified cases in the European Union and Norway. Rates in the individual countries ranged between 87.9% in Austria and 33.3% in France. *Salmonella enterica* subspecies *enterica* serovar Typhimurium (*Salmonella* Typhimurium) was second, causing 16.5% of all cases. Rates in the individual countries ranged between 5.8% in Austria and 28.7% in Ireland. As in previous years, after *Salmonella* Enteritidis and *Salmonella* Typhimurium, most cases were caused by *Salmonella enterica* subspecies *enterica* serovar Virchow (*Salmonella* Virchow), *Salmonella enterica* subspecies *enterica* serovar Infantis (*Salmonella* Infantis) and *Salmonella enterica* subspecies *enterica* serovar Hadar (*Salmonella* Hadar). Each of these serovars is involved in less than 1% of all notified cases.

The major source of contamination is through egg and poultry meat consumption. The reduction of such risks is achieved through a combination of means all along the egg and meat production chains, such as good farming, hygienic practices and vaccination.

Community legislation on food hygiene and control of zoonoses includes a number of provisions that seek to control and prevent the *Salmonella* contamination of foodstuffs. Measures to reduce *Salmonella* prevalence in live animals are believed to be one of the most effective ways of reducing the contamination of foodstuffs and the number of human salmonellosis cases.

In 2003, the new European legislation on zoonoses was published; Regulation 2160/2003 provides for the setting of pathogen reduction targets along the food chain, mainly for animal populations, and the establishment of national control plans in order to meet these targets. *Salmonella* spp. is the primary target, in particular the serotypes considered to have public health significance. Targets will be set progressively in different animal populations: breeding flocks of *Gallus gallus*, laying hens, broilers, turkeys and slaughter pigs. Up to now, targets have been established for breeding flocks of *Gallus gallus* only (Regulation 1003/2005); the target has been set at 1%, meaning that for the end of 2009 the maximum percentage of flocks positive for *Salmonella* Enteritidis, *Salmonella* Typhimurium, *Salmonella* Infantis, *Salmonella* Hadar and *Salmonella* Virchow at the EU level will have to be 1%.

As far as breeders are concerned, Regulation 1091/2005 forbids the use of antimicrobials as control measure against *Salmonella*, whereas the use of vaccines is accepted and recommended. Conclusions and recommendations of the Scientific Panel on Biological Hazards on a request from the Commission related to the use of vaccines for the control of *Salmonella* in poultry (The EFSA Journal (2004) 114, 1-74) are largely favourable toward the use of vaccines to control *Salmonella* at the farm level. In particular, the panel's conclusions are, among others, that:

The basis for successful control of *Salmonella* infections in poultry farms are good farming and hygienic practices (including all the aspects covering feed, birds, management, cleaning and disinfection, control of rodents etc.) as well as testing and removal of positive flocks from production. Vaccination of chickens is regarded as a measure to increase the resistance of birds against *Salmonella* exposure and decrease the shedding.

There is experimental and some field evidence that a reduced level of fecal excretion and systemic invasion of *Salmonella* organisms in vaccinated birds will result in a reduced contamination of table eggs and the environment.

If a control programme is targeting in breeders of layers/broilers or laying hens and the flock prevalence is high, vaccination may be useful in reducing shedding and egg contamination. If the flock prevalence is low, vaccination may not be so useful but still could be used as one of the preventive measures to maintain a low prevalence.

There are more than 2,000 serovars of *Salmonella* bacteria.

The Kauffman and White classification permits serological varieties of the genus *Salmonella* to be differentiated from each other. This scheme differentiates isolates by determining which surface antigens are produced by the bacterium. First, the "O" antigen type is determined. "O" antigens are the polysaccharides associated with the lipopolysaccharide of the bacterial outer membrane. Once the "O" antigen group is determined, the "H" antigen is determined. The "H" antigens are proteins associated with the bacterial flagella. Salmonellas exist in two phases; a motile phase and a non-motile phase. These are also referred to as the specific and non-specific phases. Different "H" antigens are produced depending on the phase in which the *Salmonella* is found. Pathogenic strains of *Salmonella typhi* carry an additional antigen, "Vi", so-called because of the enhanced virulence of strains that produce this antigen, which is associated with a bacterial capsule.

Following the Kauffman and White classification, "O"-groups of *Salmonella* serovars are formed.

Against colonization by group C *Salmonella* in chickens, an attenuated vaccine was developed, based on deleted cya/deleted crp *Salmonella* Hadar and a deleted phoP *Salmonella* Hadar (Roland K. et al., Avian Dis., 2004, 48(3): 445-52). Although the deleted cya/deleted crp derivative induced higher levels of serum antibody, it did not provide an immune response protective against colonization by *Salmonella* Hadar.

Chacana et al. (Chacana P. A. et al., Avian Dis., 2006, 50(2): 280-3) demonstrated that *Salmonella* attenuated vaccine can elicit cross-immunity against members of the same Kauffmann-White scheme serogroup. The protection conferred by TAD *Salmonella* vac E, an attenuated *Salmonella* Enteritidis vaccine, was explored against fowl typhoid. Three groups of laying hens were vaccinated with different vaccination schedules starting on the first day of life, and afterwards were infected with $2 \times 10^5$ CFU of a virulent *Salmonella* Gallinarum strain, either at week 28 or week 52. Mortality, fecal shedding, and organ invasion of *Salmonella* Gallinarum were assessed. *Salmonella* Enteritidis vaccine was able to cross-immunize against *Salmonella* Gallinarum, both strains of the D group *Salmonella*, according to Kauffmann-White classification. At week 28, hens vaccinated with three oral doses or with two oral doses combined with one subcutaneous dose were protected by the vaccine. However, at week 52, when hens were infected 36 weeks after the final immunization, the vaccine was not able to confer protection.

Due to the great number of *Salmonella* serovars, there is a need for vaccines against *Salmonella* that are able to induce a protective immune response against more than one *Salmonella* serovar and/or against *Salmonella* of more than one Kauffmann-White classification group.

SUMMARY OF THE INVENTION

Accordingly, the present invention relates to a vaccination strategy, which is based on at least one primo-administration of an attenuated *Salmonella* immunogenic composition or vaccine and at least one boost-administration of an inactivated *Salmonella* immunogenic composition or vaccine. This vaccination strategy is useful to prevent portage of homologous and heterologous *Salmonella* in vaccinated subjects.

It is also an object of this invention to provide methods of using immunogenic compositions or vaccines in order to prevent homologous and/or heterologous *Salmonella* in avian animals, wherein at least one primo-administration of an attenuated *Salmonella* immunogenic composition or vaccine is administered to an avian animal before at least one boost-administration of an inactivated *Salmonella* immunogenic composition or vaccine a few weeks later, notably from 2 weeks to 18 weeks after the unique or first primo-administration.

It is also an object of this invention to provide methods of using immunogenic compositions or vaccines in order to prevent carriage of homologous and/or heterologous *Salmonella* in avian animals, wherein at least one primo-administration of an attenuated *Salmonella* D group immunogenic composition or vaccine is administered to an avian animal before at least one boost-administration of an inactivated *Salmonella* B group and inactivated *Salmonella* D group immunogenic composition or vaccine a few weeks later, notably from 2 weeks to 18 weeks after the unique or first primo-administration. Examples of *Salmonella* B and D groups are provided herein.

It is also an object of this invention to provide kits for vaccination of avian animals, comprising at least two vials and a package insert with administration instructions, the first vial containing an attenuated *Salmonella* immunogenic composition or vaccine and the second vial containing an inactivated *Salmonella* immunogenic composition or vaccine. Optionally, additional vials can be included, which vials comprise an attenuated *Salmonella* immunogenic composition or vaccine for multiple primo-administration and/or vials comprising an inactivated *Salmonella* immunogenic composition or vaccine for multiple boost-administration.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following detailed description.

BRIEF DESCRIPTION OF DRAWINGS

The following detailed description, given by way of example, and which is not intended to limit the invention to specific embodiments described, may be understood in conjunction with the accompanying figures, incorporated herein by reference, in which.

For FIG. 1 and FIG. 2, "Control" is the non-vaccinated control group, corresponding to G.00; "L+K" is the group vaccinated twice, firstly with the attenuated *Salmonella* vaccine and secondly with the inactivated *Salmonella* vaccine, corresponding to G.01; "Killed" is the group vaccinated only with the inactivated *Salmonella* vaccine, corresponding to G.02.

DETAILED DESCRIPTION OF THE INVENTION

Figure 1:
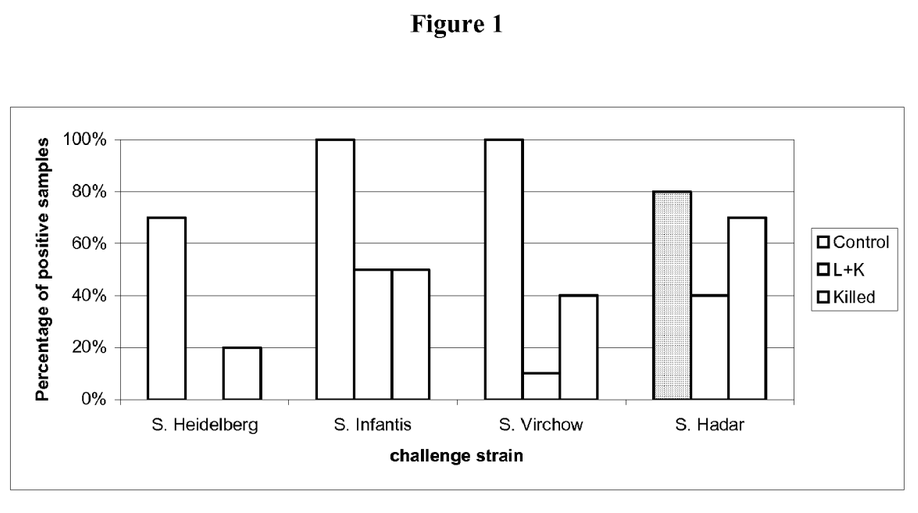
FIG. 1 illustrates the percentage of re-isolation of challenge *Salmonella* strains in the spleens of chickens, 4 to 7 days after challenge.
Figure 2:
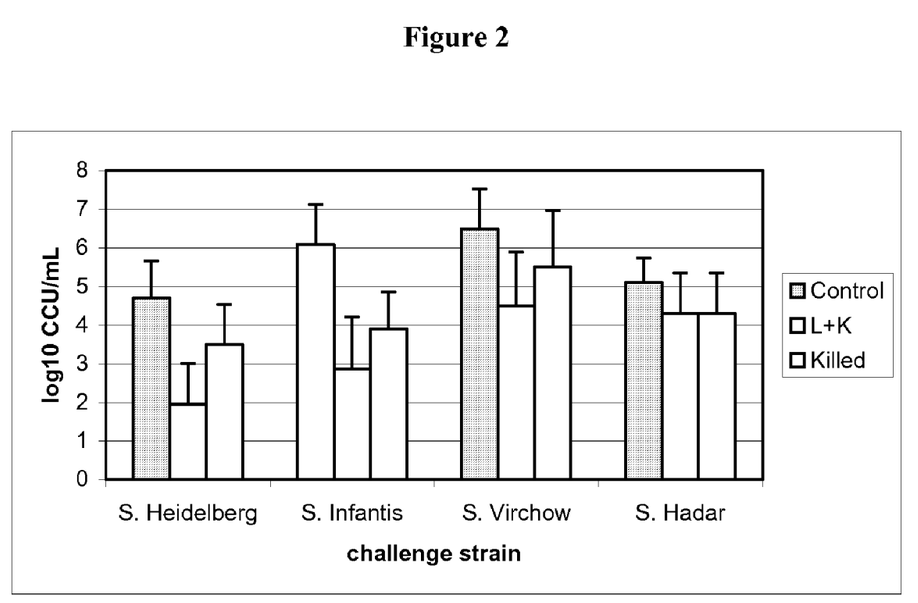
FIG. 2 illustrates the mean caecum numerations of challenge *Salmonella* strains in chickens, 4 to 7 days after challenge, and standard deviations.

The present invention relates to methods of using immunogenic compositions or vaccines in avian animals in order to increase the immune response against at least one heterologous *Salmonella*, wherein at least one primo-administration of an attenuated immunogenic composition or vaccine, comprising a pharmaceutically or veterinarily acceptable excipient, diluent or vehicle and at least one attenuated *Salmonella* of one *Salmonella* serovar, is administered to an avian animal before at least one boost-administration of an inactivated immunogenic composition or vaccine, comprising a pharmaceutically or veterinarily acceptable excipient, diluent or vehicle, and at least one inactivated *Salmonella* of one *Salmonella* serovar, a few weeks apart, notably from 2 weeks to 18 weeks apart. The attenuated *Salmonella* and the inactivated *Salmonella* may be from the same serovar or from different serovars. A heterologous *Salmonella* is a bacterium different from those used in the immunogenic compositions or vaccines administered during the primo-administration and during the boost-administration, e.g., *Salmonella* of another serovar or of another *Salmonella* group according to the Kauffmann-White classification.

The methods of the subject invention can be used in avian animals in order to cross-protect avian animals from a disease caused by at least one heterologous *Salmonella* and/or to prevent carriage of at least one heterologous *Salmonella* in avian animals.

The methods of the present invention can also be used in avian animals in order to reduce the number of *Salmonella* C group bacteria in the spleen and/or in the caeca of infected avian animals, notably to reduce the number of *Salmonella* C1 group and *Salmonella* C2 group bacteria in the spleen and/or in the caeca of infected avian animals or to reduce the number of *Salmonella* B group bacteria and of *Salmonella* C group bacteria in the spleen and in the caeca of infected avian animals. Examples of *Salmonella* C groups are provided herein.

The term "immunogenic composition" refers to any composition able, once it has been injected into an avian animal, to induce or stimulate an immune response against *Salmonella*.

The term "vaccine composition" or "vaccine" refers to any composition able, once it has been injected into an animal, especially an avian animal, to induce or stimulate a protective immune response against diseases caused by *Salmonella* and/or to induce or stimulate a protective immune response to prevent or to reduce the carriage of *Salmonella* in animals, especially avian animals.

A prime-boost regimen comprises at least one primo-administration and at least one boost administration using at least one common polypeptide, antigen, epitope or immunogen. The vaccine used in primo-administration can be different in nature than that used as a later booster vaccine. The primo-administration may comprise one or more administrations. Similarly, the boost administration may comprise one or more administrations.

The methods of the invention include at least one primo-administration and at least one boost-administration to an animal, preferably avian, of an efficient amount of the immunogenic composition or vaccine according to the invention. The animal may be male or female. This administration may be notably done by intramuscular (IM), intradermal (ID) or subcutaneous (SC) injection or via intranasal or oral administration, wherein oral administration includes, but is not limited to, administration on feed or in drinking water, gels, or sprays.

Pharmaceutically or veterinarily acceptable excipients, diluents or vehicles may be water, water for injection, saline or buffer. A stabilizer may be added to the attenuated immunogenic composition or vaccine, such as glycerine, glucide solution, like sucrose solution.

The attenuated immunogenic composition or vaccine used in the primo-administration according to the methods of the present invention comprises a pharmaceutically or veterinarily acceptable excipient, diluent or vehicle and at least one attenuated *Salmonella*. Attenuated *Salmonella* may be selected from the group consisting of *Salmonella* D group and *Salmonella* B group, preferably among the D group consisting of *Salmonella* Enteritidis, *Salmonella* Panama, *Salmonella* Dublin, *Salmonella* Gallinarum, *Salmonella* Pullorum, and among the B group consisting of *Salmonella* Typhimurium, *Salmonella* Braenderup, *Salmonella* Agona, *Salmonella* Bredeney, *Salmonella* Heidelberg, *Salmonella* Indiana, *Salmonella* Saint-Paul, *Salmonella* Brandenburg. In a preferred embodiment, the attenuated immunogenic composition or vaccine used in the primo-administration according to the methods of the present invention comprises a pharmaceutically or veterinarily acceptable excipient, diluent or vehicle and at least one attenuated *Salmonella* of D group. In another preferred embodiment, the attenuated immunogenic composition or vaccine used in the primo-administration according to the methods of the present invention comprises a pharmaceutically or veterinarily acceptable excipient, diluent or vehicle and at least one attenuated *Salmonella* of B group. In another preferred embodiment, the attenuated immunogenic composition or vaccine used in the primo-administration according to the methods of the present invention comprises a pharmaceutically or veterinarily acceptable excipient, diluent or vehicle, and at least one attenuated *Salmonella* of D group and at least one attenuated *Salmonella* of B group. In a most preferred embodiment, the attenuated immunogenic composition or vaccine used in the primo-administration according to the methods of the present invention comprises a pharmaceutically or veterinarily acceptable excipient, diluent or vehicle and attenuated *Salmonella* Enteritidis. In another most preferred embodiment, the attenuated immunogenic composition or vaccine used in the primo-administration according to the methods of the present invention comprises a pharmaceutically or veterinarily acceptable excipient, diluent or vehicle, and attenuated *Salmonella* Enteritidis and attenuated *Salmonella* Typhimurium.

Examples of various Kauffman-White *Salmonella* classification groups include the A, B, C1-3, D, E1-4, F, G, H, and I groups, examples of which are provided below.

For instance, the A group comprises *Salmonella enterica* subspecies *enterica* serovar Paratyphi A (*Salmonella* Paratyphi A), *Salmonella* Paratyphi A variant durazzo.

For instance, the B group comprises *Salmonella enterica* subspecies *enterica* serovar Paratyphi B (*Salmonella* Paratyphi B), *Salmonella* Paratyphi B variant odense, *Salmonella enterica* subspecies *enterica* serovar Java (*Salmonella* Java), *Salmonella enterica* subspecies *enterica* serovar Typhimurium (*Salmonella* Typhimurium), *Salmonella enterica* subspecies *enterica* serovar Braenderup (*Salmonella* Braenderup), *Salmonella enterica* subspecies *enterica* serovar Agona (*Salmonella* Agona), *Salmonella enterica* subspecies *enterica* serovar Bredeney (*Salmonella* Bredeney), *Salmonella enterica* subspecies *enterica* serovar Heidelberg (*Salmonella* Heidelberg), *Salmonella enterica* subspecies *enterica* serovar Indiana (*Salmonella* Indiana), *Salmonella enterica* subspecies *enterica* serovar Saint-Paul (*Salmonella* Saint-Paul), *Salmonella enterica* subspecies *enterica* serovar Brandenburg (*Salmonella* Brandenburg), *Salmonella enterica* subspecies *enterica* serovar Limete (*Salmonella* Limete), *Salmonella enterica* subspecies *enterica* serovar Agama (*Salmonella* Agama), *Salmonella enterica* subspecies

*enterica* serovar Derby (*Salmonella* Derby), *Salmonella enterica* subspecies *enterica* serovar Salinatis (*Salmonella* Salinatis), *Salmonella enterica* subspecies *enterica* serovar Stanley (*Salmonella* Stanley).

For instance, the C1 group comprises *Salmonella enterica* subspecies *enterica* serovar Paratyphi C (*Salmonella* Paratyphi C), *Salmonella enterica* subspecies *enterica* serovar Infantis (*Salmonella* Infantis), *Salmonella enterica* subspecies *enterica* serovar Mbandaka (*Salmonella* Mbandaka), *Salmonella enterica* subspecies *enterica* serovar Livingstone (*Salmonella* Livingstone), *Salmonella enterica* subspecies *enterica* serovar Virchow (*Salmonella* Virchow), *salmonella enterica* subspecies *enterica* serovar Ohio (*Salmonella* Ohio), *salmonella enterica* subspecies *enterica* serovar Montevideo (*Salmonella* Montevideo), *Salmonella enterica* subspecies *enterica* serovar Tennessee (*Salmonella* Tennessee), *Salmonella enterica* subspecies *enterica* serovar Rissen (*Salmonella* Rissen), *Salmonella enterica* subspecies *enterica* serovar Decatur (*Salmonella* Decatur), *Salmonella enterica* subspecies *enterica* serovar Bareilly (*Salmonella* Bareilly), *Salmonella enterica* subspecies *enterica* serovar Menston (*Salmonella* Menston), *Salmonella enterica* subspecies *enterica* serovar Oranienburg (*Salmonella* Oranienburg), *Salmonella enterica* subspecies *enterica* serovar Thompson (*Salmonella* Thompson).

For instance, the C2 group comprises *Salmonella enterica* subspecies *enterica* serovar Hadar (*Salmonella* Hadar), *Salmonella enterica* subspecies *enterica* serovar Newport (*Salmonella* Newport), *Salmonella enterica* subspecies *enterica* serovar Kottbus (*Salmonella* Kottbus).

For instance, the C3 group comprises *Salmonella enterica* subspecies *enterica* serovar Kentucky (*Salmonella* Kentucky), *Salmonella enterica* subspecies *enterica* serovar Albany (*Salmonella* Albany).

For instance, the D group comprises *Salmonella enterica* subspecies *enterica* serovar Typhi (*Salmonella* Typhi), *Salmonella enterica* subspecies *enterica* serovar Enteritidis (*Salmonella* Enteritidis), *Salmonella enterica* subspecies *enterica* serovar Panama (*Salmonella* Panama), *Salmonella enterica* subspecies *enterica* serovar Dublin (*Salmonella* Dublin), *Salmonella enterica* subspecies *enterica* serovar Gallinarum (*Salmonella* Gallinarum), *Salmonella enterica* subspecies *enterica* serovar Pullorum (*Salmonella* Pullorum), *Salmonella enterica* subspecies *enterica* serovar Ndolo (*Salmonella* Ndolo), *Salmonella enterica* subspecies *enterica* serovar Miami (*Salmonella* Miami), *Salmonella enterica* subspecies *enterica* serovar Sendai (*Salmonella* Sendai).

For instance, the E1 group comprises *Salmonella enterica* subspecies *enterica* serovar Give (*Salmonella* Give), *Salmonella enterica* subspecies *enterica* serovar Anatum (*Salmonella* Anatum), *Salmonella enterica* subspecies *enterica* serovar London (*Salmonella* London), *Salmonella enterica* subspecies *enterica* serovar Meleagridis (*Salmonella* Meleagridis).

For instance, the E2 group comprises *Salmonella enterica* subspecies *enterica* serovar Cambridge (*Salmonella* Cambridge), *Salmonella enterica* subspecies *enterica* serovar Newington (*Salmonella* Newington).

For instance, the E3 group comprises *Salmonella enterica* subspecies *enterica* serovar Minneapolis (*Salmonella* Minneapolis).

For instance, the E4 group comprises *Salmonella enterica* subspecies *enterica* serovar Simsbury (*Salmonella* Simsbury), *Salmonella enterica* subspecies *enterica* serovar Senftenberg (*Salmonella* Senftenberg).

For instance, the F group comprises *Salmonella enterica* subspecies *enterica* serovar Aberdeen (*Salmonella* Aberdeen).

For instance, the G group comprises *Salmonella enterica* subspecies *enterica* serovar Cubana (*Salmonella* Cubana), *Salmonella enterica* subspecies *enterica* serovar Poona (*Salmonella* Poona).

For instance, the H group comprises *Salmonella enterica* subspecies *enterica* serovar Heves (*Salmonella* Heves), *Salmonella enterica* subspecies *enterica* serovar Onderstepoort (*Salmonella* Onderstepoort).

For instance, the I group comprises *Salmonella enterica* subspecies *enterica* serovar Brazil (*Salmonella* Brazil), *Salmonella enterica* subspecies *enterica* serovar Hvittingfoss (*Salmonella* Hvittingfoss).

Some attenuated *Salmonella* vaccines and some inactivated *Salmonella* vaccines are commercially available.

U.S. Pat. Nos. 7,045,122; 6,923,957; 6,905,691; 6,605,285; 5,843,426; 5,733,760; 5,424,065; 5,389,368; and 6,592,869 relate to *Salmonella* vaccines, including attenuated and inactivated vaccines.

*Salmonella* species can be rationally attenuated by introducing non-reverting defined mutations into the genome to produce live vaccine strains. Several genes have been identified, which when mutated, will attenuate Salmonellae. In particular, *salmonella* strains harboring non-reverting mutations in genes involved in the pre-chorismate biosynthetic pathway make excellent oral vaccines evoking strong humoral, local and cellular immune responses in the host (Chatfield S. N. et al., Vaccine, 1989, 7(6): 495-8; Chatfield S. N. et al., FEMS Immunol. Med. Microbiol., 1993, 7(1): 1-7), in aro genes of the aromatic biosynthetic pathway (EP-B1-0322237), in the transcriptional regulator RfaH mutants of *Salmonella* Typhimurium, which are efficient as attenuated oral vaccines against salmonellosis in mice (Nagy G. et al., Infect. Immun., 2006, 74(10): 5914-25).

*Salmonella* may be attenuated by modification of the genome structure of the bacteria, such as by deletion of part of a *Salmonella* gene, by insertion of heterologous nucleotide sequence into a *Salmonella* gene, and/or by substitution of part of a *Salmonella* gene by heterologous nucleotide sequence. It is possible to attenuate *Salmonella* by introducing mutations that (i) confer auxotrophy, (ii) interfere with sugar metabolism and Lipopolysaccharides biosynthesis or (iii) affect some global means of regulating genes needed for a full display of virulence.

For example, attenuated *Salmonella* may be bacteria comprising at least one streptomycin and one rifampicin resistance metabolism drift mutation for the attenuation (EP-B1-0642796), such as the attenuated strain of *Salmonella* Enteritidis Sm 24/Rif 12/Ssq (EP-B1-0642796); attenuated *Salmonella* Enteritidis by a first mutation in the phoP regulatory region causing constitutive expression of a gene under the control of said region and by a second mutation at a pag or prg gene (EP-B1-0563311); attenuated *Salmonella* Enteritidis by a non-reverting mutation in the htrA gene (U.S. Pat. No. 5,804,194); attenuated *Salmonella* that exhibits auxotrophy to one or more growth factors selected from the group consisting of phenylalanine, tyrosine, tryptophan and para-aminobenzoic acid, such that it is incapable of growing on a minimal medium in the absence of said one or more growth factors (U.S. Pat. No. 6,231,871), such as *Salmonella* Typhimurium strain STM-1, deposited at the Australian Government Analytical Laboratories under Accession number N93/43266 (U.S. Pat. No. 6,231,871); auxotrophic mutants of *Salmonella* Enteritidis derived through N-methyl-N'-nitro-N-nitrosoguanidine mutagenesis, such as E 3/49 strain, 1/37 strain, C7/1 strain, C7/2 strain, C7/18 strain, C7/19 strain, E1/23 strain, E1/25 strain, E2/7 strain, E3/44 strain, and E3/51 strain (Martin G. et al., Berl. Münch. Tierärztl. Wschr., 1996, 109(10): 325-9); attenuated *Salmonella* Typhimurium harboring a non-reverting mutation in each of two discrete aro genes of the aromatic biosynthetic pathway, such as aroA and aroC, aroA and aroD, aroA and aroE (EP-B1-0322237); attenuated *Salmonella* Enteritidis genetically-defined aroC derivative (LVR02 strain, see Betancor L. et al., Vet. Microbiol., 2005, 107(1-2): 81-9); and attenuated *Salmonella* Typhimurium having a mutation that inactivates a gene selected from: hupA, dksA, rfaY, sipC or clpB (WO-A1-98/02523).

Attenuating mutations can also be obtained by insertion of a transposon. For example, the transposon in the mutant EZ870 is inserted in a *Salmonella* Enteritidis nucleotide sequence that is homologous (98.4% of identical basepairs in a 188 bp overlap) to the *Salmonella* Typhimurium gene spiC (Accession number U51927, Ochman H., Soncini F. C. Solomon F. and Groisman E. A., Proc. Natl. Acad. Sci. U.S.A. 93, 7800-7804, 1996). The genetically modified *Salmonella* enteritidis EZ870 has the deposit number LMGP-18484 at the BCCM/LMG Culture Collection, Laboratorium voor Microbiologie, Ledeganckstraat 35, B-9000 Gent, Belgium (WO-A-99/37759).

The inactivated immunogenic composition or vaccine used in the boost-administration according to the methods of the present invention comprises a pharmaceutically or veterinarily acceptable excipient, diluent or vehicle and at least one inactivated *Salmonella*. The inactivated *Salmonella* may be selected from the group consisting of *Salmonella* E group, *Salmonella* D group, *Salmonella* C group and *Salmonella* B group, preferably among the group consisting of *Salmonella* E1 group, *Salmonella* E4 group, *Salmonella* D group, *Salmonella* C1 group, *Salmonella* C2 group, *Salmonella* C3 group and *Salmonella* B group, and more preferably from among the E1 group consisting of *Salmonella* Anatum, among the E4 group consisting of *Salmonella* Senftenberg, among the D group consisting of *Salmonella* Enteritidis, *Salmonella* Panama, *Salmonella* Dublin, *Salmonella* Gallinarum, *Salmonella* Pullorum, among the C1 group consisting of *Salmonella* Infantis, *Salmonella* Mbandaka, *Salmonella* Livingstone, *Salmonella* Virchow, *salmonella* Ohio, *salmonella* Montevideo, *Salmonella* Tennessee, *Salmonella* Rissen, among the C2 group consisting of *Salmonella* Hadar, *Salmonella* Newport, *Salmonella* Kottbus, among the C3 group consisting of *Salmonella* Kentucky, *Salmonella* Albany, and from among the B group consisting of *Salmonella* Typhimurium, *Salmonella* Braenderup, *Salmonella* Agona, *Salmonella* Bredeney, *Salmonella* Heidelberg, *Salmonella* Indiana, *Salmonella* Saint-Paul, *Salmonella* Brandenburg.

In a preferred embodiment, the inactivated immunogenic composition or vaccine used in the boost-administration according to the methods of the present invention comprises a pharmaceutically or veterinarily acceptable excipient, diluent or vehicle and at least one inactivated *Salmonella* of B group and at least one inactivated *Salmonella* of D group. In another preferred embodiment, the inactivated immunogenic composition or vaccine used in the boost-administration according to the methods of the present invention comprises a pharmaceutically or veterinarily acceptable excipient, diluent or vehicle and at least one inactivated *Salmonella* of B group, at least one inactivated *Salmonella* of C group and at least one inactivated *Salmonella* of D group. In a most preferred embodiment, the inactivated immunogenic composition or vaccine used in the boost-administration according to the methods of the present invention comprises a pharmaceutically or veterinarily acceptable excipient, diluent or vehicle and inactivated *Salmonella* Typhimurium and inactivated *Salmonella* Enteritidis. In another most preferred embodiment, the inactivated immunogenic composition or vaccine used in the boost-administration according to the methods of use of the present invention comprises a pharmaceutically or veterinarily acceptable excipient, diluent or vehicle and inactivated *Salmonella* Typhimurium and inactivated *Salmonella* Enteritidis and at least one inactivated *Salmonella* of C2 group. In another most preferred embodiment, the inactivated immunogenic composition or vaccine used in the boost-administration according to the methods of the present invention comprises a pharmaceutically or veterinarily acceptable excipient, diluent or vehicle and inactivated *Salmonella* Typhimurium and inactivated *Salmonella* Enteritidis and at least one inactivated *Salmonella* of C2 group and at least one inactivated *Salmonella* of C1 group.

The *Salmonella* may be chemically inactivated by treatment with inactivating agents, such as formaldehyde, ethyleneimine, ethyleneimine amide derivatives (for example acetylethyleneimine), propyleneimine, β-propiolactone, thimerosal, acetone or heat-inactivation. In a preferred embodiment, the inactivating agent is formaldehyde.

In certain aspects, preferred methods of using immunogenic compositions or vaccines in avian animals according to the invention comprise at least one primo-administration of an attenuated immunogenic composition or vaccine, comprising a pharmaceutically or veterinarily acceptable excipient, diluent or vehicle and at least one attenuated *Salmonella* of D group, administered to an avian animal before at least one boost-administration of an inactivated immunogenic composition or vaccine, comprising a pharmaceutically or veterinarily acceptable excipient, diluent or vehicle, at least one inactivated *Salmonella* of B group and at least one inactivated *Salmonella* acceptable excipient, diluent or vehicle, at least one inactivated *Salmonella* of B group, at least one inactivated *Salmonella* of C1 group, at least one inactivated *Salmonella* of C2 group and at least one inactivated *Salmonella* of D group, a few weeks apart, such as from 2 weeks to 18 weeks apart. In a particular embodiment of this preferred method, attenuated D group *Salmonella* bacteria are *Salmonella* Enteritidis, inactivated B group *Salmonella* bacteria are *Salmonella* Typhimurium, inactivated D group *Salmonella* bacteria are *Salmonella* Enteritidis, inactivated C2 group *Salmonella* bacteria are *Salmonella* Hadar and inactivated C1 group *Salmonella* bacteria are *Salmonella* Virchow and/or *Salmonella* Infantis.

Other preferred methods of using immunogenic compositions or vaccines in avian animals according to the invention comprise at least one primo-administration of an attenuated immunogenic composition or vaccine, comprising a pharmaceutically or veterinary acceptable excipient, diluent or vehicle and at least one attenuated *Salmonella* of D group and at least one attenuated *Salmonella* of B group, administered to an avian animal before at least one boost-administration of an inactivated immunogenic composition or vaccine, comprising a pharmaceutically or veterinarily acceptable excipient, diluent or vehicle, at least one inactivated *Salmonella* of B group and at least one inactivated *Salmonella* of D group, a few weeks apart, such as from 2 weeks to 18 weeks apart. In a particular embodiment of this preferred method, attenuated D group *Salmonella* bacteria are *Salmonella* Enteritidis, attenuated B group *Salmonella* bacteria are *Salmonella* Typhimurium, inactivated B group *Salmonella* bacteria are *Salmonella* Typhimurium and inactivated D group *Salmonella* bacteria are *Salmonella* Enteritidis.

Other preferred methods of using immunogenic compositions or vaccines in avian animals according to the invention comprise at least one primo-administration of an attenuated immunogenic composition or vaccine, comprising a pharmaceutically or veterinarily acceptable excipient, diluent or vehicle and at least one attenuated *Salmonella* of D group and at least one attenuated *Salmonella* of B group, administered to an avian animal before at least one boost-administration of an inactivated immunogenic composition or vaccine, comprising a pharmaceutically or veterinarily acceptable excipient, diluent or vehicle, at least one inactivated *Salmonella* of B group, at least one inactivated *Salmonella* of C2 group and at least one inactivated *Salmonella* of D group, a few weeks apart, notably from 2 weeks to 18 weeks apart. In a particular embodiment of this preferred method, attenuated D group *Salmonella* bacteria are *Salmonella* Enteritidis, attenuated B group *Salmonella* bacteria are *Salmonella* Typhimurium, inactivated B group *Salmonella* bacteria are *Salmonella* Typhimurium, inactivated D group *Salmonella* bacteria are *Salmonella* Enteritidis and inactivated C2 group *Salmonella* bacteria are *Salmonella* Hadar.

Other preferred methods of using immunogenic compositions or vaccines in avian animals according to the invention comprise at least one primo-administration of an attenuated immunogenic composition or vaccine, comprising a pharmaceutically or veterinarily acceptable excipient, diluent or vehicle and at least one attenuated *Salmonella* of D group and at least one attenuated *Salmonella* of B group, administered to an avian animal before at least one boost-administration of an inactivated immunogenic composition or vaccine, comprising a pharmaceutically or veterinarily acceptable excipient, diluent or vehicle, at least one inactivated *Salmonella* of B group, at least one inactivated *Salmonella* of C1 group, at least one inactivated *Salmonella* of C2 group and at least one inactivated *Salmonella* of D group, a few weeks apart, such as from 2 weeks to 18 weeks apart. In a particular embodiment of this preferred method, attenuated D group *Salmonella* bacteria are *Salmonella* Enteritidis, attenuated B group *Salmonella* bacteria are *Salmonella* Typhimurium, inactivated B group *Salmonella* bacteria are *Salmonella* Typhimurium, inactivated D group *Salmonella* bacteria are *Salmonella* Enteritidis, inactivated C2 group *Salmonella* bacteria are *Salmonella* Hadar and inactivated C1 group *Salmonella* bacteria are *Salmonella* Virchow and/or *Salmonella* Infantis.

Adjuvant(s) may be added to the bacterial suspension, notably obtained after culture and inactivation. An adjuvant may be chosen from aluminium hydroxide, saponine, any water-in-oil emulsion or oil-in-water emulsion which is compatible with avian tissues (see e.g., Herbert W. J., The Lancet, 1965, Oct. 16: 771; Brugh M. et al., Am. J. Vet. Res., 1983, 44(1): 72-5; Boersma W. J. A. et al., 44$^{th}$ Forum in Immunology, "Characteristics and use of new-generation adjuvants", 503-511; Gast et al., Avian Diseases, 1993, 37 (4): 1085-91; Stone, Avian Diseases, 1993, 37: 399-405; Stone et al., Avian Diseases, 1990, 34: 979-983; Stone et al., Avian Diseases, 1983, 27(3): 688-697; U.S. Pat. No. 3,919,411; WO-A-05/009462, all herein incorporated by reference).

Examples of adjuvants include, but are not limited to, oil-in-water, water-in-oil-in-water emulsions based on mineral oil and/or vegetable oil and non ionic surfactants such as block copolymers, TWEEN® (polysorbate), SPAN® (sorbitan monoester). Such emulsions are notably those described in page 147 of "Vaccine Design—The Subunit and Adjuvant Approach", Pharmaceutical Biotechnology, 1995, volume 6, edited by Michael F. Powell and Mark J. Newman, Plenum Press, New York and London, or TS emulsions, notably the TS6 emulsion, and LF emulsions, notably LF2 emulsion (for both TS and LF emulsions, see WO-A-04/024027). Other suitable adjuvants are, for example, vitamin E, saponins, and polymers of crosslinked acrylic or methacrylic acid, i.e. CARBOPOL® (carbomer) (Noveon; see WO-A-99/51269; WO-A-99/44633), HAVLOGEN® (carbomer), aluminium hydroxide or aluminium phosphate ("Vaccine Design, The subunit and adjuvant approach", Pharmaceutical Biotechnology, vol. 6, Edited by Michael F. Powell and Mark J. Newman, 1995, Plenum Press New York), biological adjuvants (e.g., C4b, notably murine C4b (Ogata R T et al., J. Biol. Chem. 1989, 264(28): 16565-16572) or equine C4b, GM-CSF, notably equine GM-CSF (U.S. Pat. No. 6,645,740)), toxins (e.g., cholera toxins CTA or CTB, *Escherichia coli* heat-labile toxins LTA or LTB (Olsen C W et al., Vaccine, 1997, 15(10): 1149-1156; Fingerut E et al., Vaccine, 2005, 23(38): 4685-4696; Zurbriggen R et al., Expert Rev Vaccines, 2003, 2(2): 295-304; Peppoloni S et al., Expert Rev Vaccines, 2003, 2(2): 285-293)), and CpG (e.g., CpG #2395 (see Jurk M et al., Immunobiology 2004, 209(1-2): 141-154), CpG #2142 (see SEQ. ID. NO: 890 in EP-B1-1,221,955), CpG #2135, CpG #2007, CpG #2336). Polymers of crosslinked acrylic or methacrylic acid, especially crosslinked by polyalkenyl ethers of sugars or polyalcohols are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g., vinyls, allyls and other ethylenically unsaturated groups. The unsaturated radicals can also contain other substituents, such as methyl. Products sold under the name CARBOPOL® (carbomer) are especially suitable. They are crosslinked by allyl saccharose or by allyl pentaerythritol. Among them, reference is made to CARBOPOL® (carbomer) 974P, 934P, 934, 940 and 971P.

The immunogenic compositions and vaccines according to the invention may be freeze-dried advantageously with a stabilizer. Freeze-drying can be done according to well-known standard freeze-drying procedures. The pharmaceutically or veterinarily acceptable stabilizers may be carbohydrates (e.g., sorbitol, mannitol, lactose, sucrose, glucose, dextran, trehalose), sodium glutamate (Tsvetkov T et al., Cryobiology 1983, 20(3): 318-23; Israeli E et al., Cryobiology 1993, 30(5): 519-23), proteins such as peptone, albumin, lactalbumin or casein, protein containing agents such as skimmed milk (Mills C K et al., Cryobiology 1988, 25(2): 148-52; Wolff E et al., Cryobiology 1990, 27(5): 569-75), and buffers (e.g. phosphate buffer, alkaline metal phosphate buffer). An adjuvant may be used to make soluble the freeze-dried preparations.

Examples of useful oils include, but are not limited to, mineral oil, such as paraffin oil, DRAKEOL® (mineral oil) 6VR, MARCOL® 80(mineral oil); MARCOL® 52(mineral oil); terpene oils such as squalene and squalane; vegetable oils such as soybean oil, olive oil, corn oil, jojoba oil, peanut oil, cotton-seed oil, sunflower oil, safflower oil, sesame oil, apricot oil, avocado oil, wheat germ oil, canola oil, Linseed oil, and almond oil; fish oils such as shark oil, orange roughy oil, Menhaden oil, and cod liver oil; animal oils such as mink oil, lard oil, and chicken fat oil.

Examples of surfactants used in emulsion vaccines include ARLACEL® 80 (sorbitan monooleate), TWEEN® 80 (Polysorbate 80), SPAN® 80 (Sorbitan monooleate), SPAN® 85 (Sorbitan trioleate), ARLACEL® 83 (sorbitan sesquicleate), ARLACEL® 85 (sorbitan sesquioleate), and TWEEN® 61 (polyoxyethylene sorbitan), for example. Surfactants suitable for animal and vegetable water-in-oil vaccines include crude yellow, and purified beeswax, for example. Furthermore, surfactants suitable for vaccines containing squalene and squalane include ARLACEL® (sorbitan sesquioleate) and TWEEN® 80 (Polysorbate 80).

Preferably, the adjuvant is an oil to form a water-in-oil emulsion comprising a paraffin oil and surfactants, notably a paraffin oil, a polyol and fatty acid ester, and an ethoxylated polyol and fatty acid ester.

Avian animals that may be vaccinated by a method of the present invention include chickens, hens, turkeys, ducks, ducklings, geese, goslings, guinea fowls, pheasants, bantams, quails, pigeons.

The methods of the present invention relate to at least one primo-administration of an attenuated *Salmonella* immunogenic composition or vaccine and at least one boost-administration of an inactivated *Salmonella* immunogenic composition or vaccine. A one-day-old avian animal can be vaccinated by a method according to the present invention, that is to say that the unique or the first primo-administration can be administered to a one-day-old avian animal. Preferably, the unique or the first primo-administration is administered to avian animals aged from one day to about 28 days, and more preferably aged from one day to about 15 days. When at least two primo-administrations are administered, these primo-administrations are administered preferably from 2 to 4 weeks apart. The boost-administration is administered from 2 to 18 weeks after the unique or first primo-administration, preferably from 3 to 10 weeks after the unique or first primo-administration, and more preferably from 3 to 6 weeks after the unique or first primo-administration. When at least two boost-administrations are administered, these boost-administrations are administered preferably from 2 to 12 weeks apart.

In a preferred embodiment, the methods of the present invention comprise two primo-administrations and two boost-administrations. The primo-administrations are administered preferably from 2 to 4 weeks apart. The first boost-administration is administered from 6 to 10 weeks after the first primo-administration, and preferably from 8 to 10 weeks after the first primo-administration. The second boost-administration is administered from 14 to 18 weeks after the first primo-administration, and preferably from 15 to 16 weeks after the first primo-administration.

In another preferred embodiment, the methods of the present invention comprise two primo-administrations and one boost-administration. The primo-administrations are administered preferably from 2 to 4 weeks apart. The boost-administration is administered from 6 to 18 weeks after the first primo-administration, and preferably from 6 to 16 weeks after the first primo-administration, and more preferably from 11 to 16 weeks after the first primo-administration.

In another preferred embodiment, the methods of the present invention comprise one primo-administration and two boost-administrations. The first boost-administration is administered from 2 to 10 weeks after the primo-administration, and preferably from 3 to 6 weeks after the primo-administration. The second boost-administration is administered from 12 to 18 weeks after the primo-administration, and preferably from 14 to 16 weeks after the primo-administration.

In another preferred embodiment, the methods of the present invention comprise one primo-administration and one boost-administration. The boost-administration is administered from 2 to 18 weeks after the primo-administration, and preferably from 3 to 10 weeks after the primo-administration, and more preferably from 3 to 6 weeks after the primo-administration.

Suitable routes of administration of immunogenic compositionsor vaccines according to the methods of the present invention for primo-administration include oral routes, e.g., by drinking water, or ocular routes, e.g., by nebulization.

Doses of attenuated immunogenic compositions or vaccines for primo-administration according to the methods of the present invention include from about 0.1 mL to about 2.0 mL, preferably from about 0.2 mL to about 1.0 mL, and more preferably from about 0.4 mL to about 0.6 mL. These doses have from about $10^6$ colony forming unit per dose (CFU/dose) to about $10^{10}$ CFU/dose of each *Salmonella* strain, and preferably about $10^8$ CFU/dose of each *Salmonella* strain. When an attenuated immunogenic composition or vaccine is administered with drinking water to an avian animal, these doses are diluted from about 1 mL to about 5 mL of drinking water per avian animal.

Suitable routes of administration of immunogenic compositions or vaccines according to the methods of the present invention for boost-administration include subcutaneous (SC) routes and intramuscular (IM) routes. An immunogenic composition or vaccine according to the methods of the present invention can be administered by a syringe with a needle or by a needle-free apparatus (such as, for example, Pigjet, Avijet, Dermojet, Vitajet or Biojector (Bioject, Oregon, USA), see US-A-2006/0034867).

Doses of inactivated immunogenic compositions or vaccines for boost-administration according to the methods of the present invention can be from about 0.05 mL to about 2.0 mL, preferably from about 0.1 mL to about 1.0 mL, and more preferably from about 0.2 mL to about 0.4 mL. These doses have from about $10^6$ CFU/dose before inactivation to about $10^{10}$ CFU/dose before inactivation of each *Salmonella* strain, and preferably about $10^8$ CFU/dose before inactivation of each *Salmonella* strain.

Another aspect of the invention is a kit for vaccination of avian animals according to the present invention. In one embodiment, the kit comprises at least two vials and a package insert with administration instructions, the first vial comprises an attenuated *Salmonella* immunogenic composition or vaccine for primo-administration according to the methods of the present invention and the second vial comprises an inactivated *Salmonella* immunogenic composition or vaccine for boost-administration according to the methods of the present invention. Optionally, the kit can comprise vials that comprise an attenuated *Salmonella* immunogenic composition or vaccine for multiple primo-administration and/or vials that comprise an inactivated *Salmonella* immunogenic composition or vaccine for multiple boost-administration.

In another embodiment, the kit for vaccination of avian animals comprises at least two vials and a package insert with administration instructions, the first vial comprising an attenuated *Salmonella* D group immunogenic composition or vaccine and the second vial comprising an inactivated *Salmonella* B group and inactivated *Salmonella* D group immunogenic composition or vaccine. Optionally, the kit can comprise vials that comprise an attenuated *Salmonella* D group immunogenic composition or vaccine for multiple primo-administration and/or vials that comprise an inactivated *Salmonella* B group and inactivated *Salmonella* D group immunogenic composition or vaccine for multiple boost-administration.

The invention will now be further described by way of the following non-limiting examples.

Example 1

For the production of the attenuated vaccine, an adenine/histidine auxotrophic double-marker mutant of *Salmonella* Enteritidis phage type 4 (PT4) strain, derived through N-methyl-N'-nitro-N-nitrosoguanidine mutagenesis, was used. This strain of *Salmonella* was named E 3/49 strain (Martin G. et al., Berl. Münch. Tierärztl. Wschr., 1996, 109(10): 325-9). The *Salmonella* E 3/49 strain was cultured in nutrient medium containing yeast extract, Tryptone, $Na_2HPO_4 \times 2H_2O$, $MgSO_4 \times 7H_2O$ and water for injection, pH 7.6±0.2, for 18-24 hours at 37° C.±1° C. as a non-aerated culture. The cultures were stabilized with 10 vol. % glycerine, filled into containers in aliquots of 1.8 ml and stored at −80° C.±5° C.

The same nutrient medium added with glucose was used for fermentation of the bacterial strain. The cultures were non-aerated cultures for 8 to 24 hours or shake flask cultures for 8-16 hours at 37° C.±1° C. The inoculum was 0.2-10 vol. %.

The cultures were stored for +2° C. to +8° C. for up to 4 days.

The bacteria obtained were harvested and diluted with buffered physiological saline depending on the organism count and 20 vol. % saccharose solution (maximum concentration 60%). The pH of the vaccine was adjusted to 7.0±0.5 with NaOH or $CH_3COOH$.

The bacterial suspension was then lyophilized for storage.

The trays were cooled to 0° C. step-wise from the bottom upwards. The vaccine was frozen in the lyophilizer at a minimum temperature of −40° C. for approximately 3-4 hours. Once the necessary vacuum was attained the main drying process was initiated (tray temperature controlled to a maximum of +10° C.), until a product temperature of +5° C. was reached. Secondary drying then followed at a tray temperature of maximum +35° C. for a maximum of 12 hours.

After drying, the bottles were flooded with dry, sterile nitrogen, were automatically sealed, burnished and stored in a cool room.

In the attenuated vaccine obtained after reconstitution in 0.5 mL of drinking water for avian animal, the titre of attenuated *Salmonella* Enteritidis was $10^8$ colony forming unit (CFU) per dose.

Example 2

For the production of the inactivated vaccine, two different strains of *Salmonella* were used, *Salmonella* Enteritidis PT 4 strain and *Salmonella* Typhimurium DT 104 strain.

Each strain of *Salmonella* was cultured in trypticase soya broth in soft agar 0.25% (TSA).

The bacteria obtained were harvested, diluted in water for injection and frozen at a target temperature of −70° C. in bags in the presence of cryoprotectant (20% of glycerol and 5% of sucrose) for storage.

For the inactivation of *Salmonella* Enteritidis PT 4 strain, bags containing *Salmonella* Enteritidis PT 4 strain were thawed, and the bacterial suspension was transferred into a sterile vessel. The inactivating agent, formaldehyde solution 35%, was added at a concentration of 3.88% (formaldehyde solution volume/culture volume) to the bacterial suspension. After blending by stirring, the suspension was transferred into another sterile vessel. The inactivation was carried out under stirring for 24 hours at 24° C.

For the inactivation of *Salmonella* Typhimurium DT 104 strain, the same process, as described for *Salmonella* Enteritidis PT 4 strain, was carried out.

The inactivated bacteria were stored at a temperature of +5° C.+/−3° C. until use for formulation.

The inactivated *Salmonella* Enteritidis PT 4 bacteria and the inactivated *Salmonella* Typhimurium DT 104 bacteria were mixed and formulated with a water-in-oil emulsion adjuvant comprising a paraffin oil, a polyol and fatty acid ester, and a ethoxylated polyol and fatty acid ester.

A preservative was added in the finished product (i.e, thimerosal) at a final concentration of 100 μg per mL.

In the inactivated vaccine, the titre of *Salmonella* Enteritidis PT 4 strain was $10^{8.3}$ CFU/dose before inactivation, and those of *Salmonella* Typhimurium DT 104 strain was $10^8$ CFU/dose before inactivation.

Example 3

30 one-day-old SPF (specific pathogen free) chickens were randomly taken on D0 of the study, then assigned to three groups of 10 chickens each.

The groups are defined as follows:

G.00=control group

G.01=attenuated vaccine of example 1 (1 day of age)+inactivated vaccine of example 2 (21 days of age)

G.02=inactivated vaccine of example 2 (21 days of age)

After identification, each group was allocated to isolating units till D53.

On D0, animals of G.01 group were vaccinated with one dose (at least $10^8$ CFU) of attenuated vaccine of example 1 of 0.5 mL by oral route, delivered directly in the oral cavity.

At D21, the animals of G.01 and G.02 groups were vaccinated with one dose of inactivated vaccine of example 2 by intramuscular route in the left breast muscular deep region, 0.3 mL/dose, *Salmonella* Enteritidis titre $10^{8.3}$ CFU per dose before inactivation, *Salmonella* Typhimurium titre $10^8$ CFU per dose before inactivation.

The G.01 group was vaccinated last, to avoid cross contamination with the attenuated vaccine strain.

All groups were bled on D49 just before challenge, then sera collected were tested for specific antibodies. The G.00, G.01 and G.02 groups were tested by IDEXX ELISA test and by Slow Agglutination Test (SAT).

The day before challenge (D48), one aliquot of *Salmonella* Heidelberg (group B *Salmonella*), was thawed at room temperature, then suspended in 100 mL of Bio Mérieux Tryptone Soya Broth medium (TSB) and incubated at 37° C. for 14 hours.

The obtained bacterial suspension was centrifuged and the strain pellet is seeded in a fresh pre-warmed TSB and incubated at 37° C. for an optimal growth period (5 hours).

As soon as the titre of the developing bacterial culture evaluated by optical density (measured at 620 nm) was high enough to be a suspension titrating $10^9$ CFU/0.2 mL, it was used for infection of the chickens.

Serial 10 fold dilutions in TSB of the inocula were seeded on Trypticase Soya Agar (TSA) and incubated 24 hours at 37° C. for counting with 3 repeats.

On D49, all groups were challenged with *Salmonella* Heidelberg broth culture, titrating $10^{8.9}$ CFU in 0.2 ml. Each chicken was infected by oral route.

Four days post-infection (D53), all chickens were euthanized. The spleen and caecum were sampled aseptically on each chicken and placed in previously identified individual tubes. The tubes, at the end of the harvest, were processed for *Salmonella* re-isolation.

each spleen was ground into 10 mL syringe and diluted in 10 mL of buffered peptone water (BPW), 200 µl of the dilution was plated on XLT4+Ampicillin (adding at the rate of 50 µg/mL) medium for numeration (the seed was spread on the agar). The plates were incubated at 37° C. for 48 hours.

Pre-Enrichment Phase (PE)

all diluted spleens were then incubated at 37° C. for 16-20 hours, only the direct method negative spleens were proceeded completely through the next phases.

Enrichment Phase (E)

inoculation of the "PE" spleen suspension into Rappaport Vassiliadis Soya (RVS) broth at a ratio of 1:100 (5 µl in 500 µl) and incubation at 42° C. for 24 hours.

Selective Isolation plating of the "E" spleen suspension on XLT4+Ampicillin medium, then incubation at 37° C. for 48 hours—volume plated 10 Typical *Salmonella* colony was black or black center, and when this type of colony was present, the sample was scored as positive.

The results were expressed in ccu/organ.

The harvested caecal content (about 1 g) was aseptically collected in a sterile tube, weighed and diluted 1:10 weight/volume in BPW up to 10e-7.

Dilutions $10^{-2}$, $10^{-3}$, $10^{-5}$ and $10^{-7}$ were incubated at 37° C. for 16-20 hours (PE) and further treated for the enrichment phase (E) and selective isolation as for spleen samples.

*Salmonella* colonies were identified and positive plates were noted.

The re-isolation data were analysed as follows:

for spleen:
  the negative samples after pre-enrichment and enrichment were counted as 0 ccu/organ,
  the negative samples in direct plating that were positive after pre-enrichment and enrichment were counted as 10 ccu/sample, for caecal content:
  the semi-quantitative result was expressed in ccu/g of organ content, based on dilution method and positivity (i.e., 50 µl+450 µl up to dilutions $10^{-2}$, $10^{-3}$, $10^{-5}$ and $10^{-7}$ correspond, when positives, to $10^{2.3}$, $10^{3.3}$, $10^{5.3}$ and $10^{7.3}$ ccu/g of *Salmonella* caecal content respectively).

The results of specific antibody titres for all immunized and non-immunized chickens, 4 weeks after vaccination, are summarized in Table 1.

The values are expressed by geometrical mean titres (GMT) for SAT and by arithmetical mean titres (AMT) for S/N and IP *Salmonella* Enteritidis ELISA results.

TABLE 1

| Groups | SAT—GMT *SALMONELLA TYPHIMURIUM* | *SALMONELLA ENTERITIDIS* ELISA—AMT | |
|---|---|---|---|
| | | S/N Ratio | IP units |
| G.00 | <10 | 0.72 | 28 |
| G.01 | 197 | 0.37 | 63 |
| G.02 | 171 | 0.41 | 59 |

The SAT and ELISA serological results obtained from the unvaccinated group were constantly negative.

Concerning *Salmonella* Typhimurium SAT results, the inactivated vaccine alone showed consistent sero-conversion (171 SAT units) with a surprising synergic effect (15.2%) of attenuated *Salmonella* Enteritidis vaccine on *Salmonella* Typhimurium component (197 SAT units).

Regarding G.01 and G.02 *Salmonella* Enteritidis ELISA results, the AMT showed higher IP units value (6.8%) in attenuated plus inactivated vaccine than inactivated alone, 63 and 59 respectively, with 10/10 positive subjects per group.

Table 2 summarizes *Salmonella* Heidelberg re-isolation results in spleens and caecal contents 4 days post-infection (expressed as positive/total and as $\log_{10}$ ccu/spleen or g).

TABLE 2

| | Spleen | | | | Caecal content | | | | | |
|---|---|---|---|---|---|---|---|---|---|---|
| | | +/Tot. | +/Tot | $\log_{10}$ ccu | | +/Tot. a.e. dilution | | | | $\log_{10}$ ccu |
| Groups | −/Tot. | d.p. | a.e. | spleen | −/Tot. | −2 | −3 | −5 | −7 | gram |
| G.00 | 3/10 | 3/10 | 4/10 | 1.2 | 0/10 | 10/10 | 10/10 | 7/10 | 0/10 | 4.7 |
| G.01 | 10/10 | 0/10 | 0/10 | 0.0 | 2/10 | 8/10 | 1/10 | 0/10 | 0/10 | 1.9 |
| G.02 | 8/10 | 1/10 | 1/10 | 0.3 | 0/10 | 10/10 | 8/10 | 1/10 | 0/10 | 3.5 |

−: Negatives
+: Positives
d.p.: direct plating
a.e.: after enrichment

As noted in Table 3, 4 days post-infection the *Salmonella* Heidelberg challenge strain showed its ability to reach and colonize control group internal organs with 0/10 negative samples and a significant *Salmonella* numeration of 10e1.2 ccu/organ and 10e4.7 ccu/g, in spleen and caecal content respectively.

Concerning spleen results, the best protection against *Salmonella* Heidelberg challenge was given by inactivated vaccine associated with attenuated vaccine (G.01) with $\Delta=10^{1.2}$ ccu/spleen compared to control group. Significant results were achieved also in G:02 group by inactivated vaccine used alone ($\Delta=10^{0.9}$ ccu/spleen compared to control group).

Concerning caecal content results, inactivated vaccine associated with attenuated vaccine (G.01) demonstrated a very good level of protection with a $\Delta$ of $10^{2.8}$ ccu/spleen compared to the control group. The inactivated vaccine showed a significant level of caecal content protection with $\Delta=10^{1.2}$ compared to the control group.

The G.01 group serological results showed the synergic effect of attenuated vaccine injection at 1 day of age on inactivated vaccine seroconversion. The quantifiable priming effect was 6.8% for *Salmonella* Enteritidis component (63 ELISA IP units) and a surprising 15.2% for *Salmonella* Typhimurium component (197 SAT units) compared to inactivated vaccine alone.

The inactivated vaccine in association with attenuated vaccine showed a full protective effect for spleen and also against *Salmonella* Heidelberg caecal content invasion than inactivated vaccine alone, with $\Delta=10^{1.2}$ ccu/spleen and $\Delta=10^{2.8}$ ccu/gram of caecal content, compared to control results. There is a clear inter groups protection increase induced by attenuated *Salmonella* Enteritidis vaccine priming on inactivated *Salmonella* Enteritidis+*Salmonella* Typhimurium vaccine.

Example 4

The same experiment as described in example 3 was done except that the challenge *Salmonella* strain was not *Salmonella* Heidelberg but *Salmonella* Infantis.

The results of specific antibody titres for all immunized and non-immunized chickens, 4 weeks after vaccination, are summarized in Table 3.

The values are expressed by geometrical mean titres (GMT) for SAT and by arithmetical mean titres (AMT) for S/N and IP *Salmonella* Enteritidis ELISA results.

TABLE 3

| Groups | SAT—GMT *SALMONELLA* TYPHIMURIUM | *SALMONELLA ENTERITIDIS* ELISA—AMT | |
|---|---|---|---|
| | | S/N Ratio | IP units |
| G.00 | <10 | 1.27 | 00 |
| G.01 | 184 | 0.40 | 60 |
| G.02 | 139 | 0.44 | 56 |

The SAT and ELISA serological results obtained from the unvaccinated group were constantly negative.

Concerning *Salmonella* Typhimurium SAT results, inactivated vaccine alone showed consistent sero-conversion (139 SAT units) with a surprising synergic effect of attenuated *Salmonella* Enteritidis vaccine on *Salmonella* Typhimurium component (184 SAT units).

Regarding G.01 and G.02 *Salmonella* Enteritidis ELISA results, the AMT showed higher IP units value in attenuated plus inactivated vaccine than inactivated alone, 60 and 56 respectively, with 10/10 positive subjects per group.

Table 4 summarizes *Salmonella* Infantis re-isolation results in spleens and caecal contents 7 days post-infection (expressed as positive/total and as $\log_{10}$ ccu/spleen or g).

TABLE 4

| | Spleen | | | | Caecal content | | | |
|---|---|---|---|---|---|---|---|---|
| | | +/Tot. | +/Tot | $\log_{10}$ ccu | | +/Tot. a.e. dilution | | $\log_{10}$ ccu |
| Groups | −/Tot. | d.p. | a.e. | spleen | −/Tot. | −5 | −7 | gram |
| G.00 | 0/10 | 9/10 | 1/10 | 2.3 | 0/10 | 10/10 | 4/10 | 6.1 |
| G.01 | 5/10 | 3/10 | 2/10 | 0.9 | 1/10 | 1/10 | 0/10 | 2.9 |
| G.02 | 5/10 | 2/10 | 3/10 | 0.7 | 0/10 | 3/10 | 0/10 | 3.9 |

−: Negatives
+: Positives
d.p.: direct plating
a.e.: after enrichment

As noted in Table 4, 7 days post-infection the *Salmonella* Infantis challenge strain showed its ability to reach and colonize control group internal organs with 0/10 negative samples and a significant *Salmonella* numeration of $10^{2.3}$ ccu/organ and $10^{6.1}$ ccu/g, in spleen and caecal content respectively.

Concerning spleen results, a good protection against *Salmonella* Infantis challenge was given by inactivated vaccine associated with attenuated vaccine (G.01) with $\Delta=10^{1.4}$ ccu/spleen compared to control group.

Concerning caecal content results, inactivated vaccine associated with attenuated vaccine (G.01) demonstrated a very good level of protection with a $\Delta$ of $10^{3.2}$ ccu/spleen compared to control group. The inactivated vaccine showed a significant level of caecal content protection with $\Delta=10^{2.2}$ compared to control group.

The G.01 group serological results showed the synergic effect of attenuated vaccine injection at 1 day of age on inactivated vaccine seroconversion. The quantifiable priming effect was 7% for *Salmonella* Enteritidis component (60 ELISA IP units) and 32% for *Salmonella* Typhimurium component (184 SAT units) compared to inactivated vaccine alone.

Inactivated vaccine in association with attenuated vaccine showed a better protective effect mostly for caecal protection ($\Delta=10^{3.2}$ ccu/gram) and a similar protection to inactivated vaccine alone on spleens with $\Delta=10^{1.4}$ ccu/organ, compared to control results.

Example 5

The same experiment as described in example 3 was done except that the challenge *Salmonella* strain was not *Salmonella* Heidelberg but *Salmonella* Virchow.

The results of specific antibody titres for all immunized and non-immunized chickens, 4 weeks after vaccination, are summarized in Table 5.

The values are expressed by geometrical mean titres (GMT) for SAT and by arithmetical mean titres (AMT) for S/N and IP *Salmonella* Enteritidis ELISA results.

TABLE 5

| Groups | SAT—GMT SALMONELLA TYPHIMURIUM | SALMONELLA ENTERITIDIS ELISA—AMT | |
|---|---|---|---|
| | | S/N Ratio | IP units |
| G.00 | <10 | 1.07 | 00 |
| G.01 | 160 | 0.44 | 56 |
| G.02 | 149 | 0.50 | 50 |

The SAT and ELISA serological results obtained from the unvaccinated group were constantly negative.

Concerning *Salmonella* Typhimurium SAT results, the inactivated vaccine alone showed consistent sero-conversion (149 SAT units) with a surprising synergic effect of attenuated *Salmonella* Enteritidis vaccine on *Salmonella* Typhimurium component (160 SAT units).

Regarding G.01 and G.02 *Salmonella* Enteritidis ELISA results, the AMT showed higher IP units value in attenuated plus inactivated vaccine than inactivated alone, 56 and 50 respectively, with 10/10 positive subjects per group.

Table 6 summarizes *Salmonella* Virchow re-isolation results in spleens and caecal contents 4 days post-infection (expressed as positive/total and as $\log_{10}$ ccu/spleen or g).

As noted in Table 6, 4 days post-infection the *Salmonella* Virchow challenge strain showed its ability to reach and colonize control group internal organs with 0/10 negative samples and a significant *Salmonella* numeration of $10^{2.4}$ ccu/organ and $10^{6.5}$ ccu/g, in spleen and caecal content respectively.

Concerning spleen results, the best protection against *Salmonella* Virchow challenge was given by inactivated vaccine associated with attenuated vaccine (G.01) with $\Delta=10^{2.3}$ ccu/spleen compared to control group. Good results were achieved also in G:02 group by inactivated vaccine used alone ($\Delta=10^{1.8}$ ccu/spleen compared to control group).

Concerning caecal content results, inactivated vaccine in association with attenuated vaccine (G.01) demonstrated a very good level of protection with a $\Delta$ of $10^{2.0}$ ccu/spleen compared to control group. The inactivated vaccine showed a significant level of caecal content protection with $\Delta=10^{1.0}$ compared to the control group.

The G.01 group serological results showed the synergic effect of attenuated vaccine injection at 1 day of age on inactivated vaccine seroconversion. The quantifiable priming effect was 12% for *Salmonella* Enteritidis component (56 ELISA IP units) and a surprising 7.4% for *Salmonella* Typhimurium component (160 SAT units) compared to inactivated vaccine alone.

Inactivated vaccine in association with attenuated vaccine showed a better protective effect mostly for spleen protection but also against *Salmonella* Virchow caecal content invasion than inactivated vaccine alone, with $\Delta=10^{2.3}$ ccu/spleen and $\Delta=10^{2.0}$ ccu/gram of caecal content, compared to control results.

Example 6

The same experiment as described in example 3 was done except that the challenge *Salmonella* strain was not *Salmonella* Heidelberg but *Salmonella* Hadar. The final challenge inoculum titration was $10^9$ CFU/0.2 mL.

The results of specific antibody titres for all immunized and non-immunized chickens, 4 weeks after vaccination, are summarized in Table 7.

The values are expressed by geometrical mean titres (GMT) for SAT and by arithmetical mean titres (AMT) for S/N and IP *Salmonella* Enteritidis ELISA results.

TABLE 6

| | Spleen | | | | Caecal content | | |
|---|---|---|---|---|---|---|---|
| | | +/Tot. | +/Tot | $\log_{10}$ ccu | | +/Tot. a.e. dilution | | $\log_{10}$ ccu |
| Groups | −/Tot. | d.p. | a.e. | spleen | −/Tot. | −5 | −7 | gram |
| G.00 | 0/10 | 8/10 | 2/10 | 2.4 | 0/10 | 10/10 | 6/10 | 6.5 |
| G.01 | 9/10 | 0/10 | 1/10 | 0.1 | 0/10 | 5/10 | 1/10 | 4.5 |
| G.02 | 6/10 | 2/10 | 2/10 | 0.6 | 0/10 | 8/10 | 3/10 | 5.5 |

−: Negatives
+: Positives
d.p.: direct plating
a.e.: after enrichment

TABLE 7

| Groups | SAT—GMT SALMONELLA TYPHIMURIUM | SALMONELLA ENTERITIDIS ELISA—AMT | |
|---|---|---|---|
| | | S/N Ratio | IP units |
| G.00 | <10 | 0.88 | 12 |
| G.01 | 211 | 0.42 | 58 |
| G.02 | 171 | 0.49 | 51 |

The SAT and ELISA serological results obtained from the unvaccinated group were constantly negative.

Concerning *Salmonella* Typhimurium SAT results, the inactivated vaccine alone showed consistent sero-conversion (171 SAT units) with a surprising synergic effect of attenuated *Salmonella* Enteritidis vaccine on *Salmonella* Typhimurium component (211 SAT units).

Regarding G.01 and G.02 *Salmonella* Enteritidis ELISA results, the AMT showed higher IP units value (6.8%) in attenuated plus inactivated vaccine than inactivated alone, 58 and 51 respectively, with 10/10 positive subjects per group.

Table 8 summarizes *Salmonella* Hadar re-isolation results in spleens and caecal contents 4 days post-infection (expressed as positive/total and as $\log_{10}$ ccu/spleen or g).

TABLE 8

| | Spleen | | | | Caecal content | | |
|---|---|---|---|---|---|---|---|
| Groups | −/Tot. | +/Tot. d.p. | +/Tot a.e. | $\log_{10}$ ccu spleen | −/Tot. | +/Tot. a.e. dilution −5 | $\log_{10}$ ccu gram |
| G.00 | 2/10 | 4/10 | 4/10 | 1.3 | 0/10 | 9/10 | 5.1 |
| G.01 | 6/10 | 0/10 | 4/10 | 0.4 | 0/10 | 5/10 | 4.3 |
| G.02 | 3/10 | 4/10 | 3/10 | 1.1 | 0/10 | 5/10 | 4.3 |

−: Negatives
+: Positives
d.p.: direct plating
a.e.: after enrichment

As noted in Table 8, 4 days post-infection the *Salmonella* Hadar challenge strain showed its ability to reach and colonize control group internal organs with 2/10 and 0/10 negative samples and a significant *Salmonella* numeration of $10^{1.3}$ ccu/organ and $10^{5.1}$ ccu/g, in spleen and caecal content respectively.

Concerning spleen results, the best protection against *Salmonella* Hadar challenge was given by inactivated vaccine associated with attenuated vaccine (G.01) with $\Delta=10^{0.9}$ ccu/spleen compared to control group. Limited results were achieved also in G:02 group by inactivated vaccine used alone ($\Delta=10^{0.2}$ ccu/spleen compared to control group).

Concerning caecal content results, inactivated vaccine associated with attenuated vaccine (G.01) or the inactivated vaccine (G.02) demonstrated an equal level of protection with a $\Delta$ of $10^{0.8}$ ccu/spleen compared to control group.

The G.01 group serological results showed the synergic effect of attenuated vaccine injection at 1 day of age on inactivated vaccine seroconversion. The quantifiable priming effect was 14% for *Salmonella* Enteritidis component (58 ELISA IP units) and a surprising 23% for *Salmonella* Typhimurium component (211 SAT units) compared to inactivated vaccine alone.

Inactivated vaccine in association with attenuated vaccine showed a better protective effect mostly against *Salmonella* Hadar caecal content invasion than inactivated vaccine alone, compared to control results.

Table 9 summarizes the results of examples 3 to 6 regarding *Salmonella* isolation in spleens of infected chickens after challenge with *Salmonella* of heterologous serovar.

TABLE 9

Number of spleen samples for positive/negative isolation after challenge, for various treatments

| Treatment groups | Positive spleens | Negative spleens | Total |
|---|---|---|---|
| Attenuated + inactivated | 10 | 30 | 40 |
| Inactivated only | 18 | 22 | 40 |
| Total | 28 | 52 | 80 |

These results show a significant difference at 6.5% risk with the K2 test and a significant difference at 5% one-sided risk with the exact Fischer test between the group vaccinated twice according to a method of the present invention (e.g., firstly with the attenuated *Salmonella* vaccine and secondly with the inactivated *Salmonella* vaccine) and the group vaccinated only with the inactivated *Salmonella* vaccine.

The method using a primo-administration with an attenuated *Salmonella* Enteritidis vaccine (group D) enhanced the efficacy of the bivalent oily inactivated vaccine *Salmonella* Enteritidis/*Salmonella* Typhimurium against a heterologous serovar challenge from group B, and as well from groups C1 and C2 which were not present in the vaccine formulas that were employed. This enhancement is significantly shown by the reduction of spleen invasion after challenge with *Salmonella* of a heterologous serovar, by comparison with the group vaccinated twice according to a method of the present invention and the group vaccinated only with the inactivated *Salmonella* vaccine.

The invention claimed is:

1. A method comprising:
    at least one primo-administration of an attenuated immunogenic composition or vaccine, comprising a pharmaceutically or veterinarily acceptable excipient, diluent or vehicle and at least one attenuated *Salmonella*, administered to an avian animal before at least one boost-administration of an inactivated immunogenic composition or vaccine, comprising a pharmaceutically or veterinarily acceptable excipient, diluent or vehicle, and at least one inactivated *Salmonella*,
    wherein the primo-administration and boost-administration are administered between 3 and 10 weeks apart.

2. A method comprising:
    at least one primo-administration of an inactivated immunogenic composition or vaccine, comprising a pharmaceutically or veterinarily acceptable excipient, diluent or vehicle and at least one inactivated *Salmonella*, administered to an avian animal before at least one boost-administration of an attenuated immunogenic composition or vaccine, comprising a pharmaceutically or veterinarily acceptable excipient, diluent or vehicle, and at least one attenuated *Salmonella*, wherein the primo-administration and boost-administration are administered between 3 and 10 weeks apart.

3. The method of claim 1, wherein the at least one attenuated *Salmonella* or the at least one inactivated *Salmonella* is selected from the *Salmonella* B group.

4. The method of claim 3, wherein the *Salmonella* B group comprises *Salmonella* Typhimurium, *Salmonella* Braenderup, *Salmonella* Agona, *Salmonella* Bredeney, *Salmonella* Heidelberg, *Salmonella* Indiana, *Salmonella* Saint-Paul, *Salmonella* Brandenburg.

5. The method of claim 4, wherein the at least one attenuated *Salmonella* or the least one inactivated *Salmonella* of the *Salmonella* B group is *Salmonella* Typhimurium.

6. The method of claim 1, wherein the at least one attenuated *Salmonella* or the at least one inactivated *Salmonella* is selected from the *Salmonella* D group.

7. The method of claim 6, wherein the *Salmonella* D group comprises *Salmonella* Enteritidis, *Salmonella* Panama, *Salmonella* Dublin, *Salmonella* Gallinarum, *Salmonella* Pullorum.

8. The method of claim 7, wherein the at least one attenuated *Salmonella* or the at least one inactivated *Salmonella* of the *Salmonella* D group is *Salmonella* Enteritidis.

9. The method of claim 2, wherein the at least one attenuated *Salmonella* or the at least one inactivated *Salmonella* is selected from the *Salmonella* B group.

10. The method of claim 9, wherein the *Salmonella* B group comprises *Salmonella* Typhimurium, *Salmonella* Braenderup, *Salmonella* Agona, *Salmonella* Bredeney, *Salmonella* Heidelberg, *Salmonella* Indiana, *Salmonella* Saint-Paul, *Salmonella* Brandenburg.

11. The method of claim 10, wherein the at least one attenuated *Salmonella* or the least one inactivated *Salmonella* of the *Salmonella* B group is *Salmonella* Typhimurium.

12. The method of claim 2, wherein the at least one attenuated *Salmonella* or the at least one inactivated *Salmonella* is selected from the *Salmonella* D group.

13. The method of claim 12, wherein the *Salmonella* D group comprises *Salmonella* Enteritidis, *Salmonella* Panama, *Salmonella* Dublin, *Salmonella* Gallinarum, *Salmonella* Pullorum.

14. The method of claim 13, wherein the at least one attenuated *Salmonella* or the at least one inactivated *Salmonella* of the *Salmonella* D group is *Salmonella* Enteritidis.

15. The method of claim 1:

wherein the at least one attenuated *Salmonella* is a *Salmonella* of D group, the at least one inactivated *Salmonella* is a *Salmonella* of B group, further comprising at least one administration of *Salmonella* of D group between about 3 and about 10 weeks following the administration of the at least one inactivated *Salmonella* of B group.

16. The method of claim 14, wherein the attenuated D group *Salmonella* bacteria are *Salmonella* Enteritidis, inactivated B group *Salmonella* bacteria are *Salmonella* Typhimurium and inactivated D group *Salmonella* bacteria are *Salmonella* Enteritidis.

17. The method of claim 1, wherein the primo-administration and boost-administration are administered between 3 and 6 weeks apart.

18. The method of claim 2, wherein the primo-administration and boost-administration are administered between 3 and 6 weeks apart.

* * * * *

(12) EX PARTE REEXAMINATION CERTIFICATE (9529th)
United States Patent
Le Gros et al.

(10) Number: US 8,062,645 C1
(45) Certificate Issued: Feb. 25, 2013

(54) SALMONELLA VACCINE (75) Inventors: François-Xavier Le Gros, Saint Genis Laval (FR); Stephane Lemiere, Lyons (FR)

(73) Assignee: Merial Limited, Duluth, GA (US)

Reexamination Request:
No. 90/012,237, May 9, 2012

Reexamination Certificate for:
Patent No.: 8,062,645
Issued: Nov. 22, 2011
Appl. No.: 11/953,472
Filed: Dec. 10, 2007

Related U.S. Application Data

(60) Provisional application No. 60/869,524, filed on Dec. 11, 2006.

(51) Int. Cl.
*A61K 39/112* (2006.01)
*A61K 39/00* (2006.01)
*A61K 39/116* (2006.01)
*C12P 1/00* (2006.01)

(52) U.S. Cl. ............... 424/258.1; 424/184.1; 424/203.1; 424/41

(58) Field of Classification Search ........................ None
See application file for complete search history.

(56) References Cited

To view the complete listing of prior art documents cited during the proceeding for Reexamination Control Number 90/012,237, please refer to the USPTO's public Patent Application Information Retrieval (PAIR) system under the Display References tab.

*Primary Examiner* — Shri Ponnaluri (57) ABSTRACT

The present invention relates to the field of vaccination against Salmonella in animals, particularly avian animals. The present invention also encompasses kits and uses of Salmonella immunogenic compositions or vaccines. The present invention further relates to methods and compositions comprising at least one primo-administration of an attenuated immunogenic composition or vaccine, comprising a pharmaceutically or veterinarily acceptable excipient, diluent or vehicle and at least one attenuated Salmonella, administered to an avian animal before at least one boost-administration of an inactivated immunogenic composition or vaccine, comprising a pharmaceutically or veterinarily acceptable excipient, diluent or vehicle, and at least one inactivated Salmonella.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 3, 6, 9-14, 16 and 18 are cancelled.

Claims 1, 4, 5, 7 and 15 are determined to be patentable as amended.

Claims 8 and 17, dependent on an amended claim, are determined to be patentable.

New claims 19-20 are added and determined to be patentable.

1. A method comprising:
   at least one primo-administration of an attenuated immunogenic composition or vaccine, comprising a pharmaceutically or veterinarily acceptable excipient, diluent or vehicle and at least one attenuated Salmonella *of D group*, administered to an avian animal before at least one boost-administration of an inactivated immunogenic composition or vaccine, comprising a pharmaceutically or veterinarily acceptable excipient, diluent or vehicle, and at least one inactivated Salmonella *of B group and at least one inactivated Salmonella of D group*,
   wherein the primo-administration and boost-administration are administered between 3 and 10 weeks apart; *and*,
   *wherein said method cross-protects avian animals from at least one heterologous Salmonella of C group.*

4. The method of claim [3] *1*, wherein the Salmonella B group comprises Salmonella Typhimurium, [Salmonella Braenderup,] Salmonella Agona, Salmonella Bredeney, Salmonella Heidelberg, Salmonella Indiana, Salmonella Saint-Paul, Salmonella Brandenburg.

5. The method of claim 4, wherein the at least one [attenuated Salmonella or the least one] inactivated Salmonella of the Salmonella B group is Salmonella Typhimurium.

7. The method of claim [6] *1*, wherein the Salmonella D group comprises Salmonella Enteritidis, Salmonella Panama, Salmonella Dublin, Salmonella Gallinarum, Salmonella Pullorum.

15. The method of claim 1:
   [wherein the at least one attenuated Salmonella is a Salmonella of D group, the at least one inactivated Salmonella is a Salmonella of B group.]
   *further comprising at least one administration of Salmonella D group between about 3 and about 10 weeks following the administration of the at least one inactivated Salmonella of B group and at least one inactivated Salmonella of D group.*

*19. The method of claim 1, wherein said cross-protection comprises protection from an infection caused by at least one heterologous Salmonella of C group.*

*20. The method of claim 1, wherein said cross-protection comprises reducing carriage of at least one heterologous Salmonella of C group.*

\* \* \* \* \*